ns. Tips on the furcations have floss-guiding portions by means of which a floss-strand may be tensioned therebetween. A handle portion is provided on the other end of the frame. A capstan device is mounted for rotation on the frame, with supply and take-up capstan portions axially spaced thereon. Said capstan device is disposed intermediate the opposite ends of said frame, and said supply and take-up portions are on opposite sides, respectively, thereof. The handle portion has a chamber therein which opens through the side of the frame which is adjacent to the supply capstan portion. A cover slidably mounts on the handle portion in covering relation with the opening of the chamber. Detent means is provided for detachably securing the cover in closed position. A supply of floss strand is provided in the chamber. The strand is threaded through the detent means, about the supply capstan portion, across the furcations, and about the take-up capstan portion where it is secured to the capstan device. The detent means frictionally grips the strand. The threading is in a direction such that as the capstan device is rotated in one direction, the strand is tensed from the detent means about the capstan device and across the aforesaid furcations.

United States Patent [19]

Loubier

[11] Patent Number: 4,508,125
[45] Date of Patent: Apr. 2, 1985

[54] DENTAL FLOSS APPLICATOR

[76] Inventor: Robert J. Loubier, 5122 Chippewa Ct., Fort Wayne, Ind. 46804

[21] Appl. No.: 435,619

[22] Filed: Oct. 20, 1982

[51] Int. Cl.$^3$ .............................................. A61C 15/00
[52] U.S. Cl. .................................................. 132/92 R
[58] Field of Search .................... 132/92 R, 89, 90, 91, 132/92 A; 220/245

[56] References Cited

U.S. PATENT DOCUMENTS

| 2,133,651 | 1/1938 | Baker | 132/92 R |
| 3,534,745 | 10/1970 | Waters | 132/92 R |
| 3,848,613 | 11/1974 | Sheehan | 132/92 R |
| 3,908,678 | 9/1975 | Conn et al. | 132/92 A |
| 4,214,598 | 7/1980 | Lee | 220/345 |

Primary Examiner—Richard J. Apley
Assistant Examiner—Carolyn A. Harrison
Attorney, Agent, or Firm—George A. Gust

[57] ABSTRACT

An improved dental floss applicator for use in dispensing and supporting a strand of dental floss under tension for cleaning teeth comprises an elongated supporting frame having on one end two laterally spaced furca- 5 Claims, 6 Drawing Figures FIG. 6 is a cross section taken substantially along section line 6—6 of FIG. 1.

DENTAL FLOSS APPLICATOR

BACKGROUND OF THE INVENTION

1. Field of the Invention

The present invention relates to dental floss applicators for use in dispensing and supporting a strand of dental floss under tension for cleaning the teeth, and more particularly to an applicator which may be easily loaded with floss strand and the strand maintained in tension on the frame of the applicator.

2. Description of the Prior Art

The present invention is an improvement over the dental floss applicator of U.S. Pat. No. 4,214,598. Much of this prior patent is incorporated in this disclosure by reference.

SUMMARY OF THE INVENTION

The present invention constitutes an improvement over the aforesaid prior art patent in the respect of structure for loading and assuring tensioning of a floss strand on the frame of the applicator. This applicator includes an elongated supporting frame having on one end two laterally spaced furcations. Tips are provided on the furcations having floss-guiding portions by means of which a floss-strand may be tensioned therebetween. A handle portion is provided on the other end of the frame. A capstan device is mounted for rotation on the frame with supply and takeup capstan portions axially spaced thereon. The capstan device is disposed intermediate the opposite ends of the frame and the supply and takeup portions are on opposite sides, respectively, thereof. The handle portion is provided with a chamber therein which opens through the side of the frame adjacent to the supply capstan portion. A cover is slidably mounted on the handle portion in covering relation with the opening of the chamber. Detent means is provided for detachably securing the cover in closed position. A supply of floss-strand in the chamber is threaded through the detent means, about the supply capstan portion, across the furcations, about the takeup capstan portion and then secured to the capstan device. The detent means frictionally grips the strand and resists withdrawal thereof from the chamber thereby contributing to the tensing of the strand. The threading of the strand is in a direction that as the capstan device is rotated in one direction the strand is tensed from the detent means, about the capstan device and across the furcations.

It is an object of this invention to provide an improved dental floss applicator.

The above-mentioned and other features and objects of this invention and the manner of attaining them will become more apparent and the invention itself will be best understood by reference to the following description of an embodiment of the invention taken in conjunction with the accompanying drawings.

DESCRIPTION OF THE PREFERRED EMBODIMENT

Figure 1:
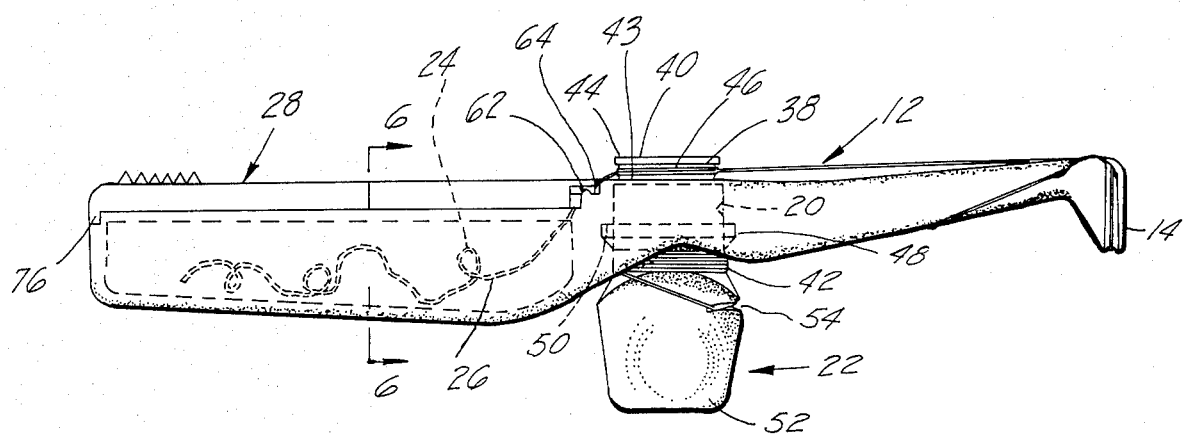
FIG. 1 is a side view of an embodiment of this invention.

Referring to the drawings, the applicator comprises an elongated, rigid body 12 formed of a suitable plastic material such as high density polyethylene. It is shaped as shown, being provided with rounded corners and edges on all parts so as to avoid chafing of the dental floss and to facilitate manipulation. Molded integrally onto one end of the body 12 are furcations 14 and 16 which are generally parallel and spaced apart laterally of the body 12. The adjacent portion of the body 12 is necked down as shown and widens at the end to provide a bridge portion 18 from which the furcations 14 and 16 extend.

About midway between the ends, the body 12 is provided with a cylindrical bearing opening 20 which frictionally receives for rotation a capstan device indicated generally by the numeral 22. The applicator thus far described coincides substantially in design with that of prior U.S. Pat. No. 4,214,598 except as otherwise shown in the drawings.

Figure 2:
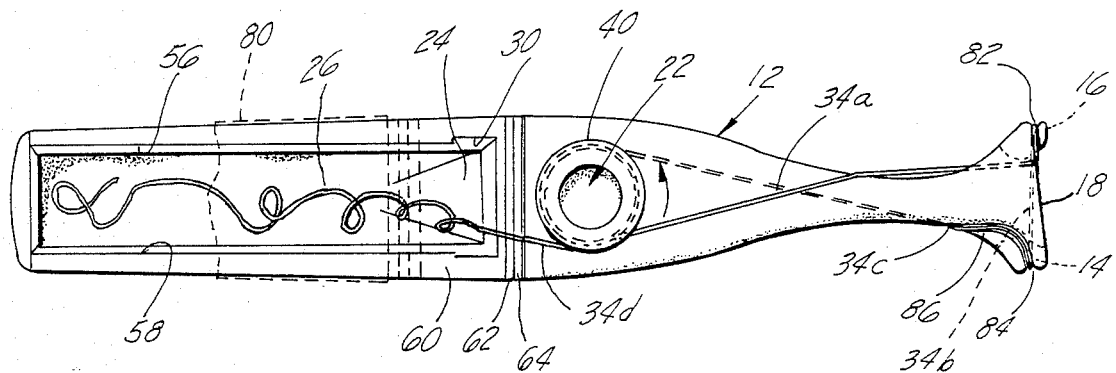
FIG. 2 is a bottom plan view thereof with the cover removed.
Figure 3:
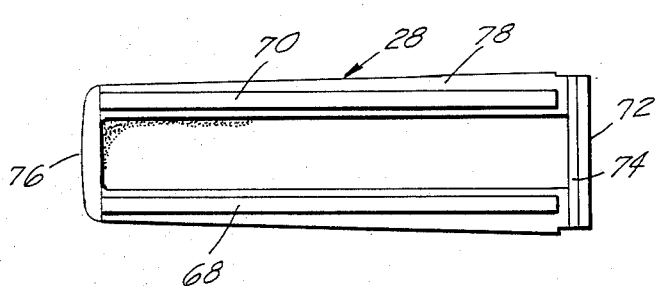
FIG. 3 is a plan view of the underside of the cover.
Figure 4:
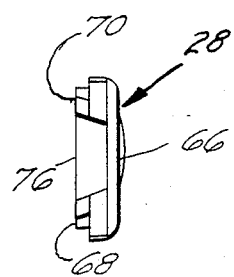
FIG. 4 is an end view thereof.
Figure 5:
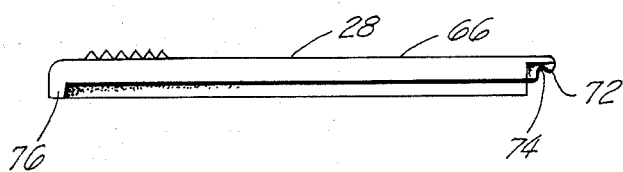
FIG. 5 is a side view thereof.

To the left side of the capstan device 22 as viewed in FIGS. 1 and 2, the body 12 is provided with an elongated cavity or chamber 24 which receives a supply of floss-strand 26 either in loose or spool form. A plastic cap 28 is slidably secured to the body 12 over the elongated opening 30 of chamber 24, which will be explained in more detail later on.

The capstan device 22 is essentially like that of prior U.S. Pat. No. 4,214,598. It is a one-piece element preferably molded, made of material hard enough to withstand the compression of floss under tension. Delrin (Dupont trademark for acetal plastic) is an appropriate material. Between the end portions, the capstan device 22 is provided with a journal bearing portion 38 which frictionally fits into the bearing opening 20. On one end is a supply capstan portion 40 and on the other end a takeup capstan portion 42. It will be noted that both portions 40 and 42 project beyond the adjacent sides of the body 12 as shown.

As is also true in the aforesaid U.S. Pat. No. 4,214,598, the axis of the capstan device 22 is canted slightly with respect to the longitudinal axis of the body 12. The supply capstan 40 is of a diameter no larger than the journal bearing 38 so that the capstan device 22 may be easily inserted into the bearing opening 20 and removed as may be desired.

The portion 40 is composed of two flanges 43 and 44 and a cylindrical barrel portion 46. The take-up capstan portion 42 also is provided with an annular flange 48 of a size larger than the bearing opening 20 to engage the flat annular surface 50 on the body 12 surrounding the opening 20. As shown more clearly in FIG. 1, a knob 52 is provided on the end of the capstan device 22 and is provided with a generally V-shaped notch 54 of a size and shape into which a strand may be force fitted for securing it to the knob. Otherwise, the notch 54 may be constructed as disclosed in the aforesaid U.S. Pat. No. 4,214,598.

Figure 6:
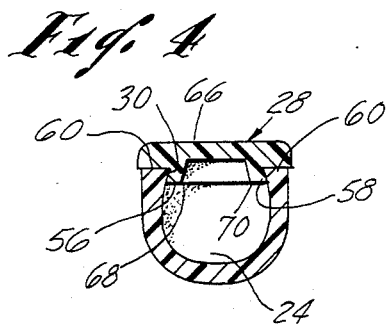

The cavity or chamber 24 is elongated and defined in part by two wall surface portions 56 and 58 which are elongated, spaced apart and extend parallel, and further are angled inwardly toward each other as shown in FIG. 6. The opening 30 further has a coplanar flat rim portion 60. The wall surface portions 56 and 58 conjointly serve as an elongated guideway as will be explained in more detail later on. Adjacent to the capstan device 22, and just ahead of the opening 30, the frame 12 is provided with two transversely extending, elongated raised and recessed portions 62 and 64 which cooperate with similarly shaped portions on the cover 28 for detachably securing the latter in closed position over the chamber opening 30.

The cover 28 has an essentially flat top 66 provided on the underside with two elongated, spaced apart and parallel, rail-like elements 68 and 70 having outer surfaces shaped to complement the wall surface portions 56 and 58 so as to be slidably engageable therewith. At the forward end of the cover 28 there is provided elongated, transversely extending raised and recessed portions 72 and 74 shaped to have a snap or detent-type fit with the recessed and raised portions, respectively, 64 and 62 on the body 12. The cover 28 is adapted to have a sliding fit in the guideway 56, 58 until the detent portion 72, 74 engages and snaps over and into mating relation with the detent portion 62, 64 on the body 12. The cover 28 is thereupon locked in place against rearward movement. Outward or lateral movement of the cover 28 is resisted by the wedge-type engagement of the guide elements 68 and 70 in the guideway 56 and 58. The aft end of the handle 12 is closed by engagement of the depending flange 76 on the cover 28 which fits into a companion notch in the frame 12 when the detent means 62, 64, 72, 74 is engaged.

The underside of the cover 28 laterally outwardly of the two elongated guide elements 68 and 70 as indicated by the numeral 78 is flat and coplanar and thereby slidably engageable with the upper flat surface 60 on the frame 12, which surrounds the chamber opening 30. Thus, the cover 28 may be slidably reciprocated along the open side of the chamber 24 into closed and open positions as desired.

The floss strand 26 is threaded on the applicator with the cover 28 slightly ajar to the dashed line position indicated by the numeral 80 in FIG. 2. The strand is wrapped two or three turns about the supply capstan portion 46 counterclockwise as shown in FIG. 2, from there along the body 12 to the furcation 16, the strand portion 34a passing on the inside of the furcation 16 around and through the groove 82 and across the span to the furcation 14. Here the strand portion 34b passes through the groove 84 along side the furcation 14, through the groove 86 at the butt portion to a position of section 34c. The section 34c then extends to and wraps around the barrel section 42 of the take-up capstan portion counterclockwise again as viewed in FIG. 2, two or more turns, the end then being forced into the groove 54 which retains the strand in place. This threading from the supply capstan portion 46 back to the take-up capstan portion 42 is substantially identical to that of prior U.S. Pat. No. 4,214,598.

After threading, the cover 28 is slid in the guideway 56, 58 forwardly until the detent portions 62, 64, 72, 74 snap into engagement which thereupon holds the cover 28 in closed position. Prior to snapping the cover 28 in position, it will be noted that the strand 26 overlies the detent portion 62, 64 on the frame 12 such that when the cover 28 is snapped in place, the strand in the region indicated by the numeral 34d is frictionally clamped or gripped between the detent portion 62, 64 on the frame 12 and the corresponding detent portion 74, 72 on the cover 28. This frictional gripping resists withdrawal of the strand 26 from the chamber 24.

In the operation of the applicator, the capstan 22 is rotated until the floss-strand across the furcations 14 and 16 is suitably tensioned. The floss is then used in the typical manner by inserting the section 34b between the teeth. Once the section 34b becomes worn, the capstan 22 is rotated about one-half turn, or in other words, sufficiently to span the furcations 14 and 16 with a new section of floss. For this adjusted position, the floss will have about the same tension as before, and no further manipulations need to be performed in order to maintain this tension, the opposed torque on the two capstan portions 40 and 42 plus the frictional fit of the journal bearing 38 in the opening 20 preventing the capstan 22 from slipping or turning. Should the floss become too highly tensioned, such tension can be reduced simply by slightly turning the capstan 22 in reverse as necessary to obtain the desired tension.

In rotating the capstan device 22 counterclockwise as shown in FIG. 2, the floss strand is tensioned as just explained and furthermore the section 34d of the strand is withdrawn from the chamber 24. Since this section 34d is frictionally gripped by the detent portions 62, 64, 72, 74, the section 34d leading to the supply capstan portion 46 is tensioned as capstan device 22 is rotated. This retains the two or three turns of the strand about the supply capstan portion 46 taut and frictionally secured thereto, or in other words, holds the strand against slippage thereon, such that the necessary tension in the strand portion 34b is retained during cleaning of the teeth. If the cover 28 is partially opened to the position 80 in FIG. 2, usage of the applicator in cleaning the teeth will soon result in the loss of tension in the portion 34b due to slippage of the strand about the supply capstan portion 46.

The detent means 62, 64, 72, 74 thus not only secures the cover 28 in place but also provides the necessary holding force on the floss-strand to tense the section 34d sufficiently to prevent or at least resist slippage of the turns on the supply capstan portion 46.

While there have been described above the principles of this invention in connection with specific apparatus, it is to be clearly understood that this description is made only by way of example and not as a limitation to the scope of the invention.

What is claimed is:

1. An improved dental floss applicator for use in dispensing and supporting a strand of dental floss under tension for cleaning teeth comprising an elongated supporting frame having on one end two laterally spaced furcations, tips on said furcations having floss-guiding portions by means of which a floss-strand may be tensioned therebetween, a handle portion on the other end of said frame, a cylindrically shaped capstan device mounted for rotation on said frame with supply and takeup capstan portions axially spaced thereon, the axis of said capstan device extending transversely to the longitudinal axis of said frame, said capstan device being disposed intermediate the opposite ends and said supply and takeup portions being on opposite sides, respectively, of said frame, said handle portion having a chamber therein which opens through the same side of said frame as said supply capstan portion, a cover mounted on said handle portion in covering relation with the opening of said chamber and slidable in opposite directions parallel to said longitudinal axis to open and close said opening, detent means interposed between said chamber and said capstan device for detachably securing said cover in closed position when said cover is moved in one longitudinal direction toward said capstan device, a supply of floss-strand in said chamber, said strand being threaded through said detent means, about said supply capstan portion, across said furcations, about said takeup capstan portion and then secured to said capstan device, said detent means retaining said cover in a chamber closing position and frictionally gripping said strand with sufficient force to resist without preventing strand movement through the detent so as to maintain the floss-strand on the supply capstan taut, and said threading being in a direction that as said capstan device is rotated in one direction said strand is tensed from said detent means, about said supply captan portion, across said furcations and about said takeup capstan portion.

2. The applicator of claim 1 wherein said chamber opening is defined by two spaced parallel elongated edges, said edges being on wall surface portions which are elongated, parallel and covergently angled thereby to provide an elongated guideway, said cover having two spaced elements which slidably engage and interlock with said guideway whereby said cover may be slidably moved relative to the chamber opening.

3. The applicator of claim 2 wherein the axis of said guideway is parallel to the longitudinal axis of said frame, said chamber having sides defined in part by said wall surface portions, said detent means including mating raised and recessed portions of said cover engageable with the recessed and raised portions of the frame to secure said cover in place, said mating portions receive and frictionally grasp said strand therebetween.

4. The applicator of claim 3 wherein said raised and recessed portions are elongated and extend transversely of said frame, said raised and recessed portions being engageable by sliding said cover in said guideway longitudinally of said frame to a position at which said chamber opening is closed.

5. The applicator of claim 4 wherein said chamber is elongated parallel to the axis of said frame, a coplanar rim surrounding said chamber opening, said cover having a copolanar rim-engaging portion that slidably engages said rim when said cover is engaged with said guideway as aforesaid.

* * * * *